United States Patent [19]
Taheri

[11] Patent Number: 5,591,159
[45] Date of Patent: Jan. 7, 1997

[54] TRANSCAVITARY MYOCARDIAL PERFUSION APPARATUS

[76] Inventor: Syde A. Taheri, 268 Dan Troy, Williamsville, N.Y. 14221

[21] Appl. No.: 336,412

[22] Filed: Nov. 9, 1994

[51] Int. Cl.$^6$ .................................................. A61B 17/36
[52] U.S. Cl. .................................................. 606/15
[58] Field of Search ........................... 606/1, 10, 11, 606/12, 13, 14, 15, 16, 17

[56] References Cited

U.S. PATENT DOCUMENTS

| | | | |
|---|---|---|---|
| 4,658,817 | 4/1987 | Hardy | 606/15 |
| 5,104,393 | 4/1992 | Isner et al. | 606/15 |
| 5,106,386 | 4/1992 | Isner et al. | 606/15 |
| 5,297,564 | 3/1994 | Love | 606/14 |
| 5,298,026 | 3/1994 | Chang | 606/15 |
| 5,368,603 | 11/1994 | Halliburton | 606/17 |
| 5,370,608 | 12/1994 | Sahota et al. | 606/17 |
| 5,454,782 | 10/1995 | Perkins | 604/20 |

*Primary Examiner*—Angela D. Sykes
*Assistant Examiner*—Sonya Harris-Ogugua
*Attorney, Agent, or Firm*—Lieberman & Nowak LLP

[57] ABSTRACT

A device for effecting myocardial perfusion is described. The described device comprises a plunger or catheter disposed within a capsule having bulbous members having appended thereto slit needles which are capable of perforating myocardium. The plunger is spring loaded and, when activated, causes the slit needles to emerge from the capsule and excise portions of the myocardium, so permitting perfusion at such sites. Perforation of the myocardium may also be affected by means of a laser beam directed through the luminia of the needle. Use of the described device eliminates long post open heart recovery, and permits patients to return to a productive life shortly after surgery.

7 Claims, 5 Drawing Sheets

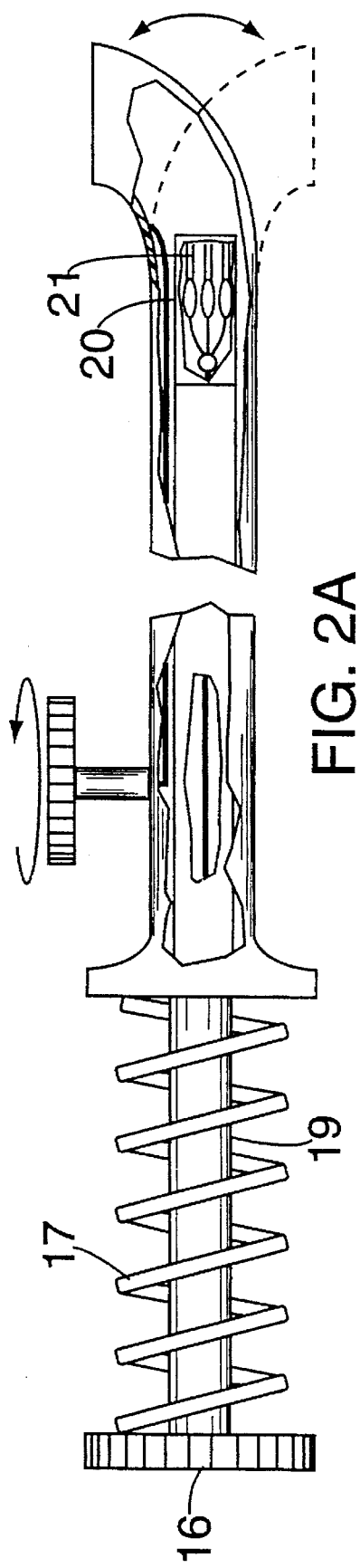
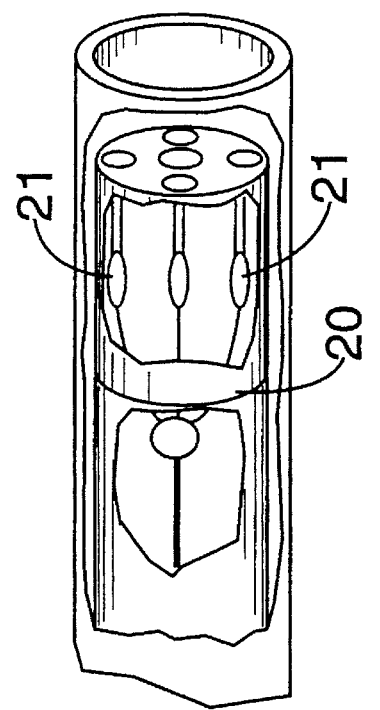
FIG. 2A
FIG. 2B

TRANSCAVITARY MYOCARDIAL PERFUSION APPARATUS

BACKGROUND OF THE INVENTION

This invention relates to a technique for the treatment of coronary artery disease. More particularly, the present invention relates to a novel procedure for enhancing myocardial perfusion during myocardial revascularization.

During the year 1992, more than 300,000 patients underwent myocardial revascularization with a mortality rate ranging from 3–5% and a morbidity costing taxpayers more than two billion dollars. In 1994, there have already been more than 600,000 cases of coronary bypass surgery with a mortality rate ranging from 2–8%. This high rate of mortality has been attributed to surgical technique, the patient's condition and post operative complications. In order to enhance the surgical procedure employed for this purpose, workers in the field have continued their pioneering efforts.

In accordance with the present invention, this end has been successively attained by a novel technique using a device which effects perfusion of the myocardium by direct puncture thereof using an image amplifier. Open heart surgery conducted in accordance with the invention eliminates the need for lengthy post open heart recovery and allows the patient to return to a productive life within a short time following surgery.

SUMMARY OF THE INVENTION

Transcavitary myocardial perfusion, referred to as "TRAC", is effected with a device comprising: (a) a thin walled sheet, introducer and guide wire; and (b) a spring handled plunger or catheter having a capsule including slit needles designed for myocardial puncture.

In the practice of the invention, under local anesthesia, image amplification and trans-femoral approach, direct puncture of the femoral artery is effected by means of needle and guide wire. The introducer and thin walled sheet are then passed over the guide wire and directed to the left ventricle of a patient. The introducer is then removed and the plunger carrying the needles is passed over the guide wire and into the left ventricle. At that juncture, the plunger is activated, so causing the needles to enter the myocardium several times. Then, satisfactory angiocardiography is performed following which the sheet and plunger are removed. Groin bleeding subsequent to the procedure is controlled by local compression.

Alternatively, perforation of the myocardium may be effected by means of a laser beam through the luminia of the needle, rather than by needle perforation, or high velocity drill.

BRIEF DESCRIPTION OF THE DRAWINGS

The invention will be more fully understood by reference to the following detailed description taken in conjunction with the accompanying drawings, wherein:

FIG. 1 (b) shows a frontal view of the heart chamber shown in FIG. 1(a) after insertion therein of the transcavitary myocardial perfusion apparatus of the present invention;

FIG. 2(a) shows a side view of the plunger or catheter of the invention, including a capsule containing slit needles;

FIG. 2(b) is a magnified view of the capsule shown in FIG. 2(a);

DETAILED DESCRIPTION OF THE INVENTION

The present invention is described in terms of its preferred embodiments. However, it will be understood that these embodiments are set forth for purposes of exposition only and are not to be construed as limiting. The numbering sequence employed in referencing device elements is consistent in each figure.

Figure 1A:
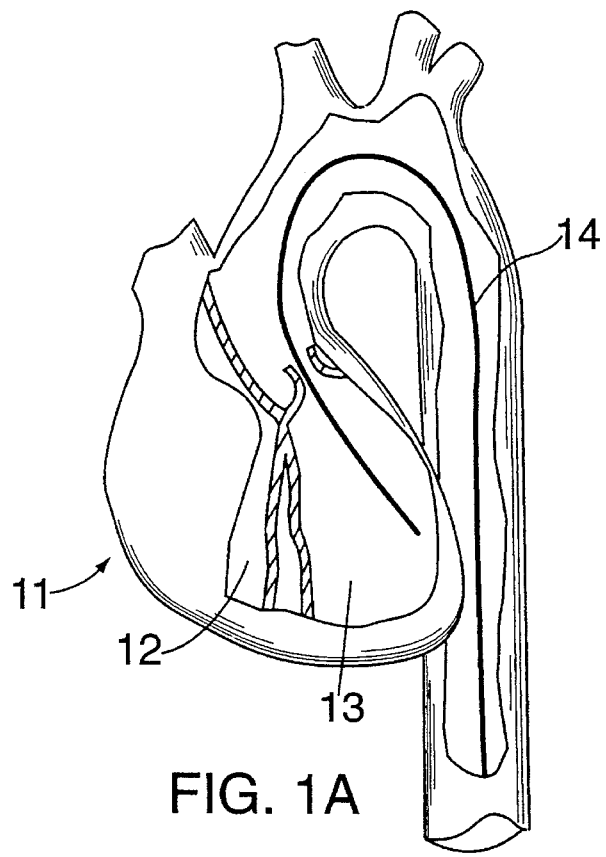
FIG. 1 (a) shows a frontal view of the left ventricle of a human heart after insertion therein of a guide wire in accordance with the invention.

With reference to FIG. 1(a), there is shown a frontal view of a heart chamber 11 in which the left ventricle 12 and an infarcted left ventricle 13 are revealed. Also shown is guide wire 14 introduced into left ventricle 13, the former serving as a guide for the subsequent introduction of the transcavitary myocardial perfusion apparatus of the invention.

Figure 1B:
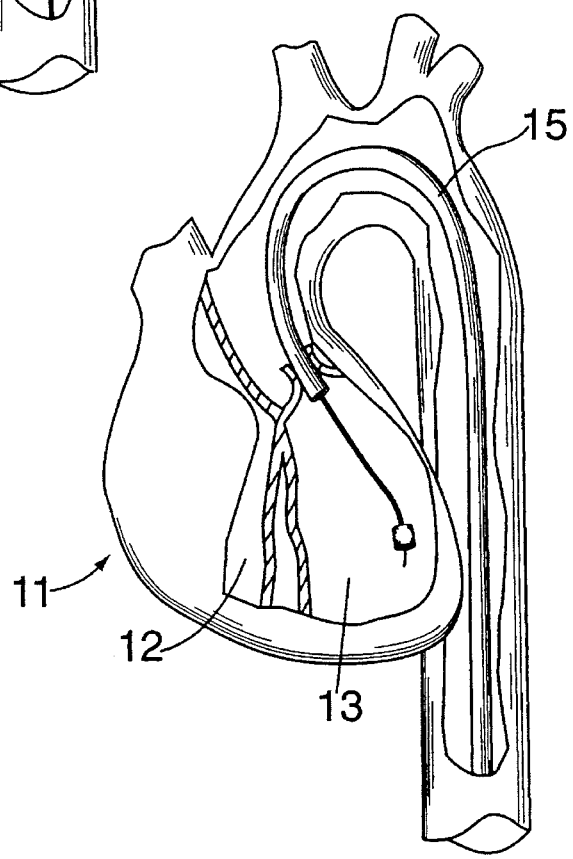

In FIG. 1(b), there is shown chamber 11 of FIG. 1(a) after insertion therein of device 15 designed to facilitate myocardial perfusion.

In FIG. 2(a), there is shown plunger 16 comprising spring member 17 attached to and in cooperation with plunger 16. Plunger 16 is comprised of a cylindrical shaft 19 having attached thereto a capsule 20 having a plurality of slit needles 21 designed to perforate the myocardium upon activation of plunger 16. FIG. 2(b) shows a magnified view of the capsule and slit needles shown in FIG. 2(a) in the non-activated state.

Figure 3A:
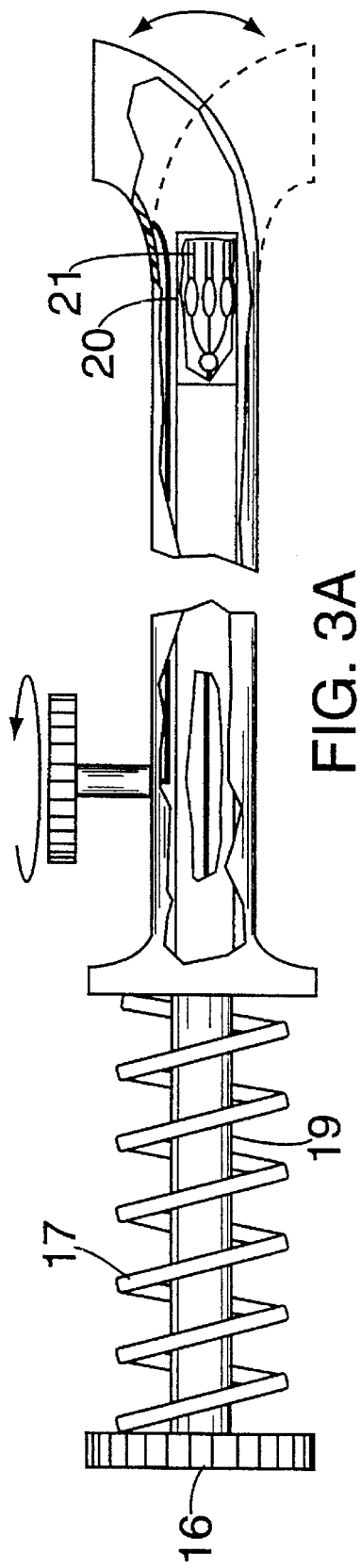
FIG. 3(a) is another side view of a non-activated plunger or catheter of the invention.
Figure 3B:
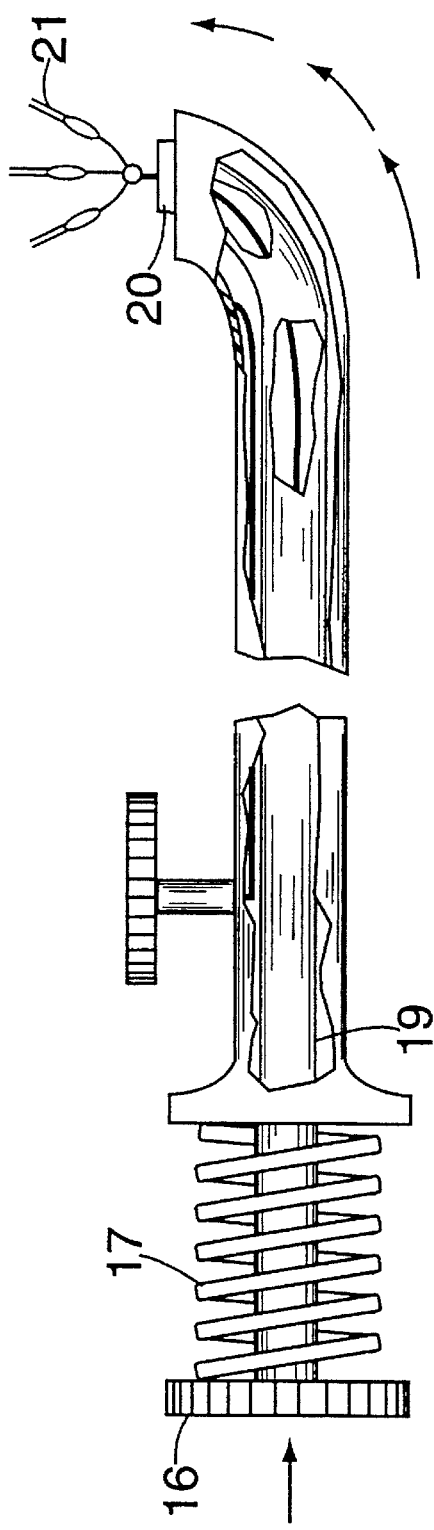
FIG. 3(b) is a side view of the plunger shown in FIG. 3(a) after activation showing the slit needles extending outward from the capsule.

FIG. 3(a) shows another side view of the non-activated plunger 16 shown in FIG. 2(a). FIG. 3(b) shows the structure of FIG. 3(a) after activation of plunger 16. Upon activation of plunger 16, spring member 18 is compressed, so causing slit needles to move forward in capsule 20 and emerge therefrom for the purpose of perforation of the myocardium.

Figure 4A:
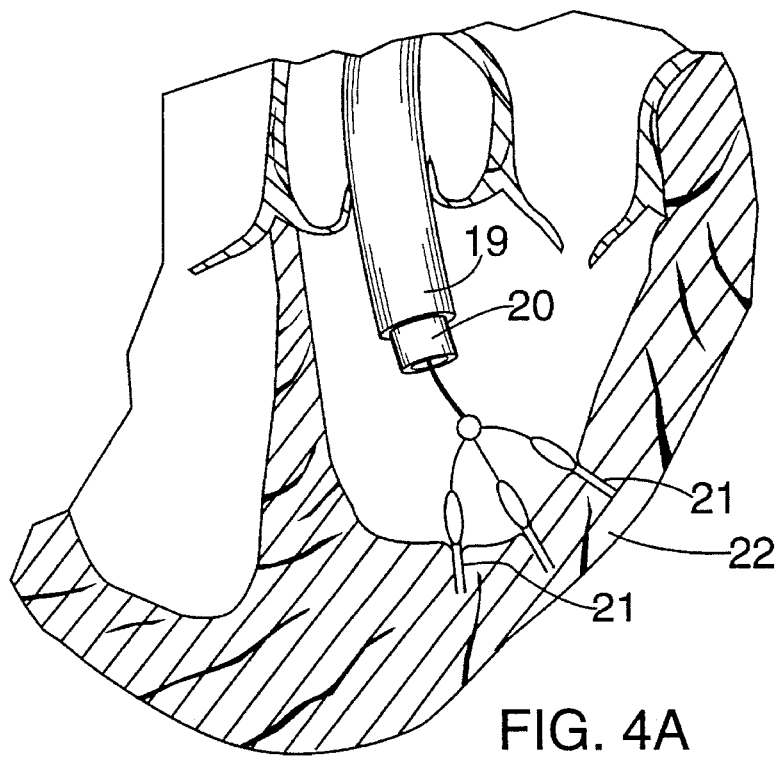
FIG. 4(a) is a side view of the activated plunger of the invention showing perforation of the slit needle into the myocardium.
Figure 4B:
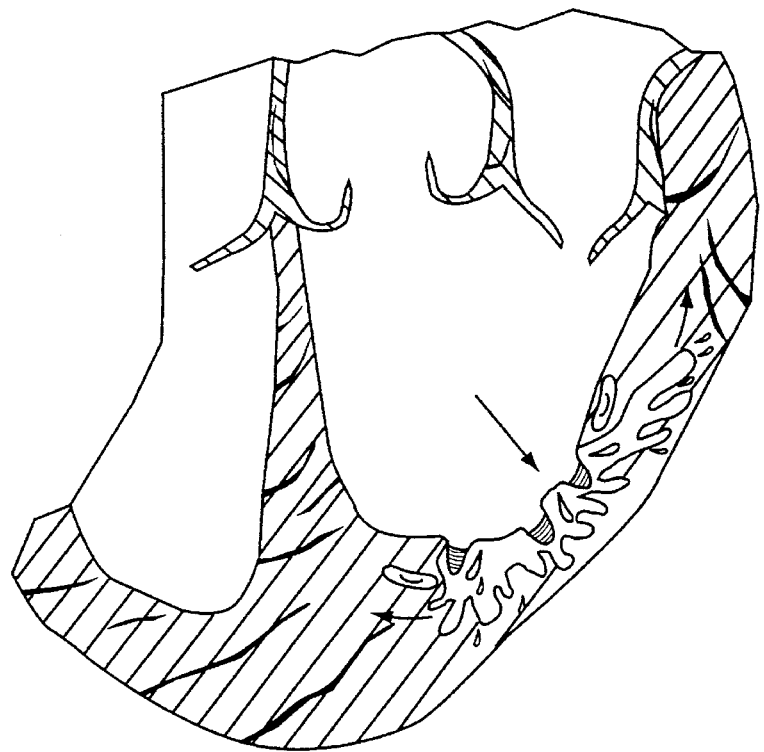
FIG. 4(b) is a view of the myocardium shown in FIG. 4(a) after withdrawal of the slit needles and perfusion of blood into the myocardium.

FIG. 4(a) shows slit needles 21 perforating the myocardium 22. This procedure is repeated several times so as to assure the formation of appropriate slits in the myocardium through which perfusion of blood will be effected. Slit needles 21 may conveniently be guided to the desired locations in myocardium 22 by means of well-known image amplification techniques.

Figure 5:
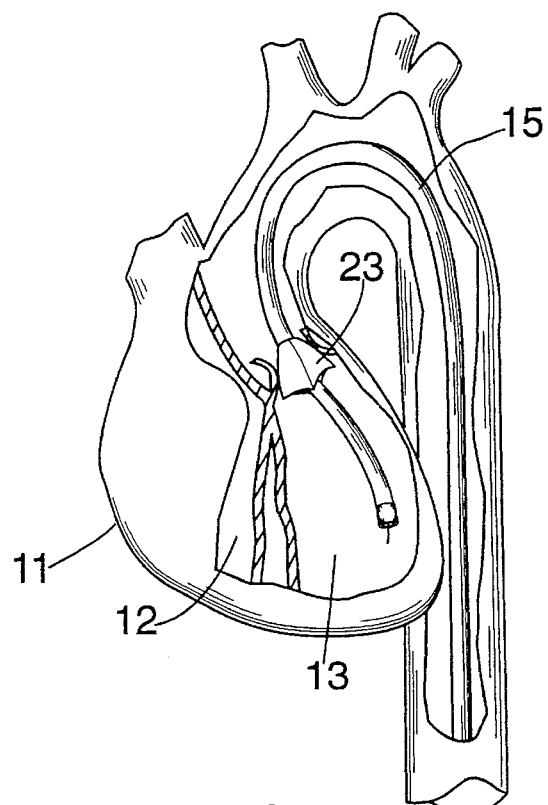
FIG. 5 is a view of the apparatus employed in the practice of the present including a protective umbrella which opens to retrieve excised muscle dislodged during needle puncture.

FIG. 5 shows a view of the apparatus shown in FIG. 1(b) further including protective umbrella 23, which may be opened to retrieve excised muscle dislodged from puncturing slit needles 21 during the perforation process.

Figure 6:
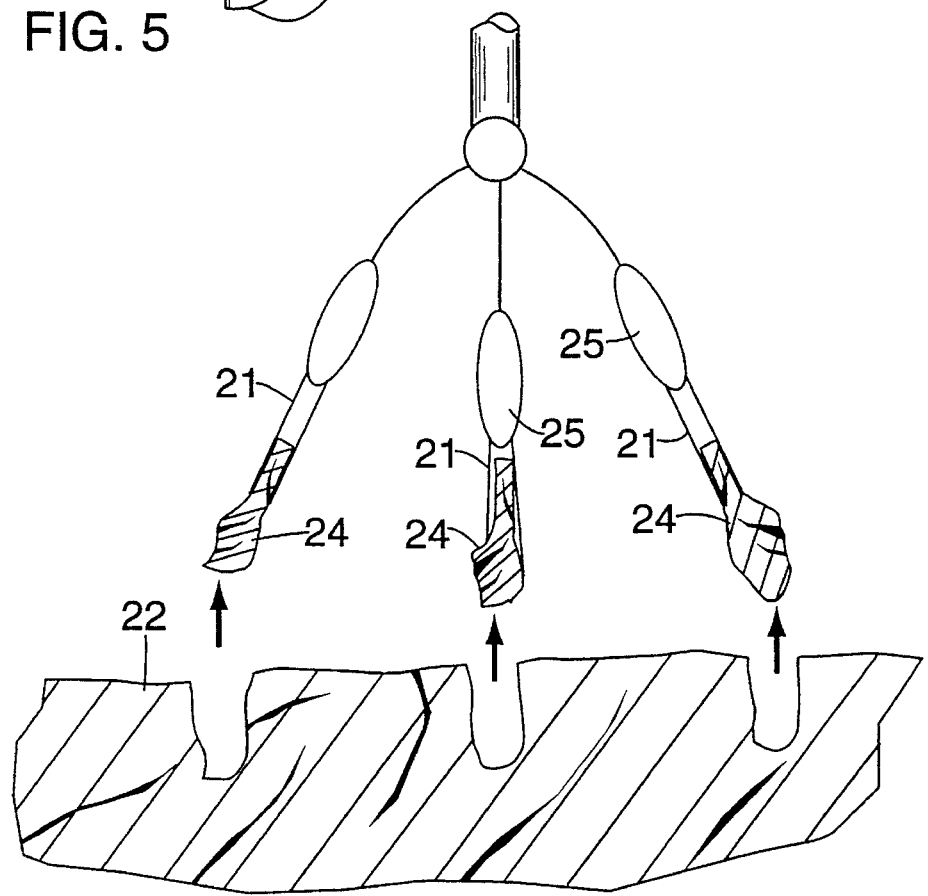
FIG. 6 is a magnified view of the slit cutting needles of the invention following excision of myocardium.

FIG. 6 shows a magnified view of slit needles 21 after perforation of the myocardium 22 and excision therefrom of excised muscle 24. In the FIGURE, spring slit needles 21 are shown positioned essentially parallel to each other and anchored in bulb 25. Upon perforation of the myocardium, small sections of muscle 24 are excised and held firmly by slit needles 21 during withdrawal from the myocardium. Any muscle 24 dislodged during the withdrawal process is retrieved by umbrella 23.

It will be understood by those skilled in the art that variations may be made without departing from the spirit and scope of the invention. Thus, for example, the needle perforation technique can be eliminated by the use of a laser beam introduced into the device which then serves as the perforation means, or automated computerized controlled myocardial perforation related to the thickness of the myocardial wall, or high velocity drill.

What is claimed is:

1. Method for the treatment of coronary artery disease which comprises the steps of:

effecting puncture of the femoral artery in the human heart by means of a needle and guide wire, passing a thin walled sheet and introducer over the guide wire and directing same to the left ventricle of a patient, removing the introducer and replacing same with a spring handled plunger having a capsule bearing a plurality of slit needles, each of which is anchored in a bulb, activating the plunger, so causing the slit needles in said capsule to move forward in a plane normal to the plunger and into the myocardium of a patient, withdrawing the plunger and the slit needles from the myocardium, and effecting perfusion of the myocardium.

2. Method in accordance with claim 1 wherein excision of myocardium is effected during activation and withdrawal of the slit needles from the myocardium.

3. Method in accordance with claim 2, wherein a protective umbrella is appended to the plunger to retrieve excised muscle dislodged during needle puncture.

4. Transcavitary myocardial perfusion device including a cylindrical body having contained therein a spring loaded plunger having a handle at one end, and a capsule at the other end, said capsule having disposed therein a plurality of bulbous members to which are affixed slit needles for effecting perforation of myocardium.

5. Device in accordance with claim 4, wherein said plunger further includes a protective umbrella which is capable of opening and retracting during operation.

6. Device in accordance with claim 4, wherein each of said bulbous members has at least two slit needles affixed thereto, which are disposed in an essentially parallel relationship to each other.

7. Device in accordance with claim 4, wherein perforation of the myocardium may be effected by means of a laser beam directed through the luminia of the needle.

* * * * *